United States Patent [19]

Dierlam

[11] Patent Number: 5,654,795
[45] Date of Patent: Aug. 5, 1997

[54] INTERNAL VISUAL WELD INSPECTION APPARATUS

[75] Inventor: Oliver T. Dierlam, Houston, Tex.

[73] Assignee: CRC-Evans Pipeline International, Inc., Houston, Tex.

[21] Appl. No.: 467,271

[22] Filed: Jun. 6, 1995

[51] Int. Cl.$^6$ ................................ G01N 21/00
[52] U.S. Cl. .................. 316/241; 356/320; 356/237; 250/559.24
[58] Field of Search .................. 355/241, 320, 355/237; 250/560

[56] References Cited

U.S. PATENT DOCUMENTS 4,275,414  6/1981  Norris .......................... 356/241
4,784,463  11/1988  Miyazaki ....................... 356/241
4,967,092  10/1990  Fraignier ....................... 356/241
5,090,608  2/1992  Jones ........................... 228/49.3

*Primary Examiner*—Frank G. Font
*Assistant Examiner*—Reginald A. Ratiff
*Attorney, Agent, or Firm*—Sidley & Austin

[57] ABSTRACT

A visual inspection apparatus (18) is disclosed for viewing welds between pipe sections (26, 28). The apparatus (18) can be part of a combination plug clamp and inspection apparatus (12) or used independently of the plug clamp (12). The TV camera (20) is aimed along the center line axis (52) of the apparatus and pipeline and a mirror (76) reflects the image of a portion of the weld into the lens of the camera. The mirror can be rotated to allow the entire circumference of the weld to be inspected. A weighted ring (102) provides a reference relative to the vertical independent of the orientation of the apparatus within the pipeline.

17 Claims, 9 Drawing Sheets

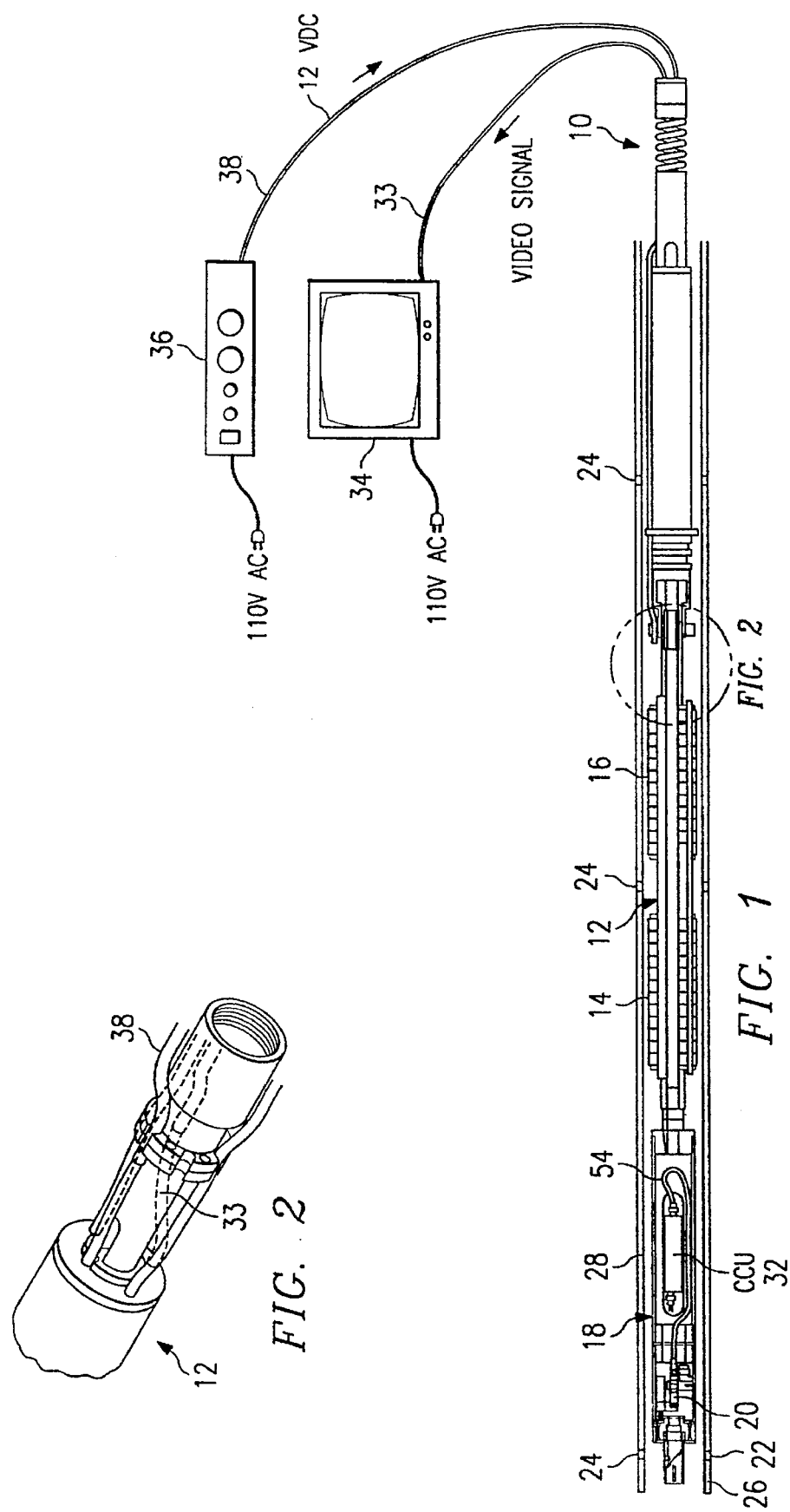

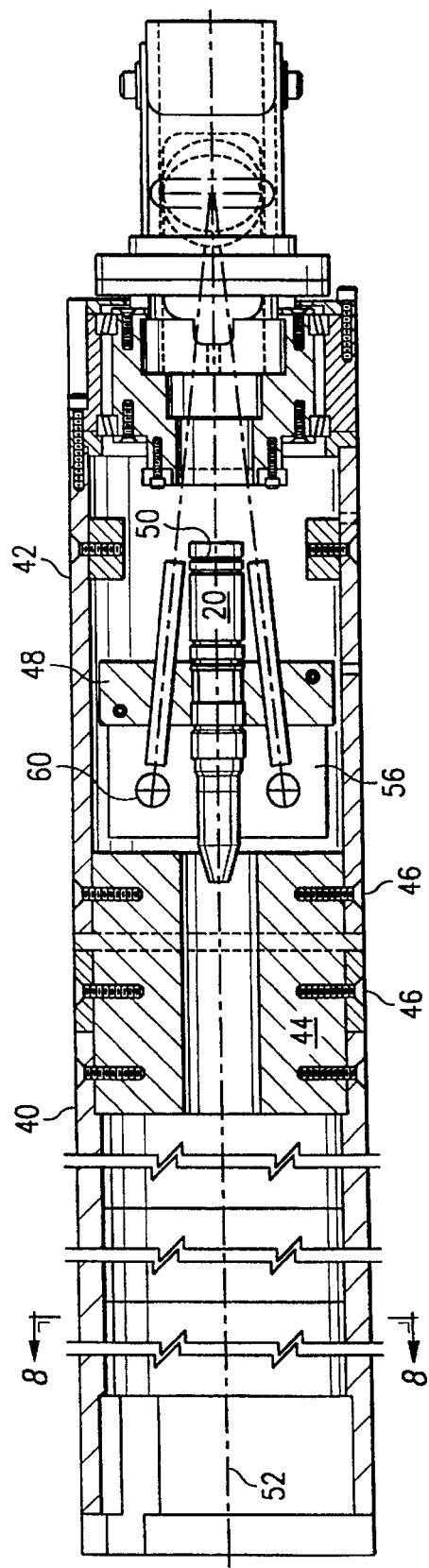
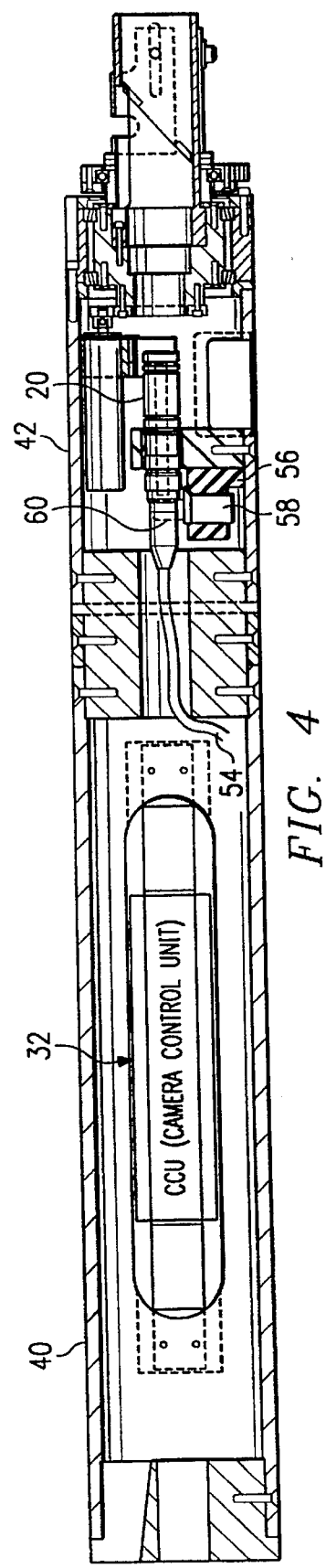
FIG. 3
FIG. 4

INTERNAL VISUAL WELD INSPECTION APPARATUS

TECHNICAL FIELD OF THE INVENTION

This invention relates to pipeline construction, in particular to welded pipe and the inspection thereof.

BACKGROUND OF THE INVENTION

A pipeline constructed of pipe sections welded together requires inspection to insure that the weld is properly made. While it is usually simple to inspect the weld outside the pipeline, it becomes more difficult to inspect the portion of the weld inside the pipeline. Visual inspection of the weld can detect weld gaps or improper welds, permitting the weld to be redone before the pipeline is pressurized.

In large pipes, it is possible for a man to actually crawl into the pipe for inspection. However, many pipelines are too small for this, and even for larger pipelines, actual inspection is a time consuming and expensive endeavor. A need therefore exists for a more efficient and cost-effective mechanism for visual inspection of welds within a pipeline.

SUMMARY OF THE INVENTION

In accordance with one aspect of the present invention, a device is provided for inspecting welds between pipe sections in a pipeline. The device includes a member sized for insertion within the interior of the pipe section and a camera mounted on the member with the lens of the camera aligned with the elongate axis of the pipeline. A mirror assembly is provided which is mounted on the member. The mirror assembly includes a mirror which reflects the image of a portion of the weld between adjacent pipe sections along the elongate axis of the pipeline into the lens of the camera.

In accordance with another aspect of the present invention, a light source can be provided on the member to illuminate the portion of the weld being examined. Further, the mirror assembly can include a mechanism to rotate the mirror about the elongate axis to examine the entire circumference of the weld between adjacent pipe sections. The light source can be transmitted through a light guide tube and the mirror assembly can be rotated by a drive motor driving a driven gear through a gear box.

BRIEF DESCRIPTION OF THE DRAWINGS

For a more complete understanding of the present invention, and for further advantages thereof, reference is now made to the following description, taken in conjunction with the accompanying drawings, in which:

FIG. 1 is a side view of a visual inspection apparatus forming a first embodiment of the present invention;

FIG. 2 is a detailed view of a portion of the apparatus illustrating the passage of cables and gas tubes through the device;

FIG. 3 is a cross-sectional side view of a portion of the apparatus illustrating the camera mounting;

FIG. 4 is a cross-sectional plan view of the apparatus illustrating the camera mounting and control unit mounting;

DETAILED DESCRIPTION

Figure 5:
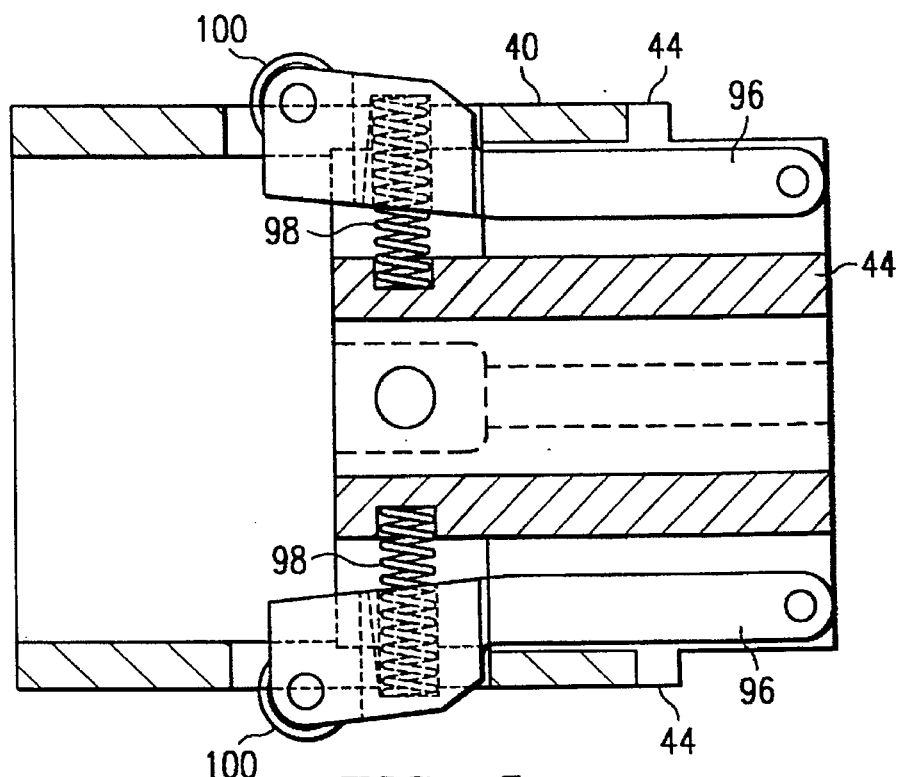
FIG. 5 is a cross-sectional view of a portion of the apparatus illustrating the alignment wheels.
Figure 8:
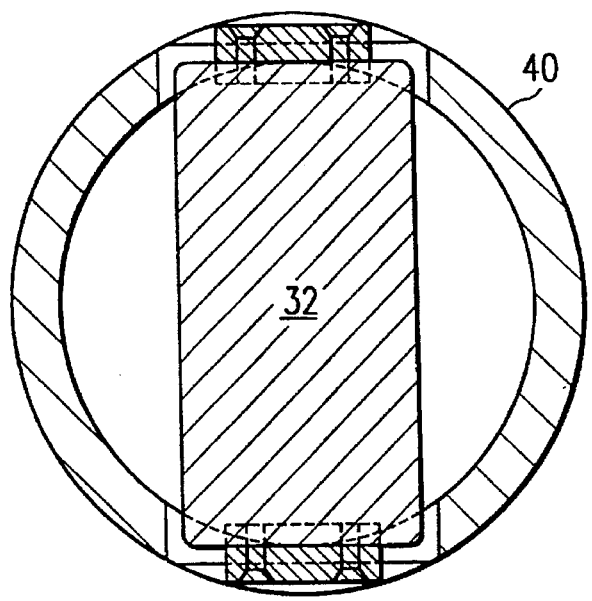
FIG. 8 is a cross section of the apparatus taken along line 8—8 in FIG. 3.

With reference now to the accompanying drawings, wherein like or corresponding parts are designated by the same reference numeral, and with specific reference to FIG. 1, a combination plug clamp and visual inspection apparatus 10 is illustrated. The apparatus 10 includes a plug or pipe clamp 12 with expandable elastomeric portions 14 and 16 which can be expanded outward into tight engagement with interior surfaces of two adjacent pipe sections to hold and align the pipe sections for welding. An apparatus of this type is described in U.S. Pat. No. 5,090,608 issued on Feb. 25, 1992 to Dick Jones, which patent is hereby incorporated by reference herein in its entirety. The apparatus may be used to inspect a pipeline of four and one-half inch inner diameter and larger, for example.

Attached to the plug clamp 12 is a visual inspection apparatus 18. As will be discussed hereinafter, the apparatus 18 includes a video monitor 34 external the pipeline to display an image of a portion 22 of the weld 24 between adjacent pipe sections 26 and 28 for inspection. A VCR recording of the image can also be made. The image is received by a camera 20 within the pipeline at the weld, transferred to a camera control unit (CCU) 32 for signal processing, with the final signal being transferred along monitor cable 33 through the plug clamp 12 to video monitor 34 outside the pipeline. A control and power supply 36, also outside the pipeline, can provide power to the apparatus 18 through power cable 38.

As can be seen, the apparatus 18 is threaded to the end of the plug clamp 12. As the plug clamp is operated to clamp adjacent pipe sections for welding, the apparatus 18 could be mounted to the clamp 12 in a manner to permit a visual inspection to be made of the weld adjacent to the weld being performed. The apparatus 18 can also be used independently of the pipe clamp 12 to inspect a pipeline already welded.

With reference to FIGS. 3–12, the apparatus 18 can be seen to include a tubular camera control unit housing 40 and a tubular camera and drive housing 42 connected by a camera housing coupling 44 through screws 46. Secured within the housing 42 is a camera mounting assembly 48 which mounts the camera 20 so that the lens 50 thereof is centered along the center line 52 of the apparatus. A signal cable 54 extends from the TV camera 20 to the camera control unit 32. Both camera 20 and camera control unit 32 are conventional and are readily available from many sources. A Toshiba Model 1KM41MA video camera would be suitable. By mounting both camera 20 and camera control unit 32 in the apparatus 18, cable 33 need only be a simple shielded cable, and can be, for example, 60 to 100 feet long.

A lamp mounting block 56 is also secured in the housing 42 behind the camera and mounts a pair of lamp assemblies 58 including light bulbs 60. Preferably, the light bulbs 60 are of the type commonly used in modern automotive lighting run off a 12-volt DC source. Control and power supply 36 can vary the intensity of the light by varying the voltage supplied to the bulbs 60.

Figure 6:
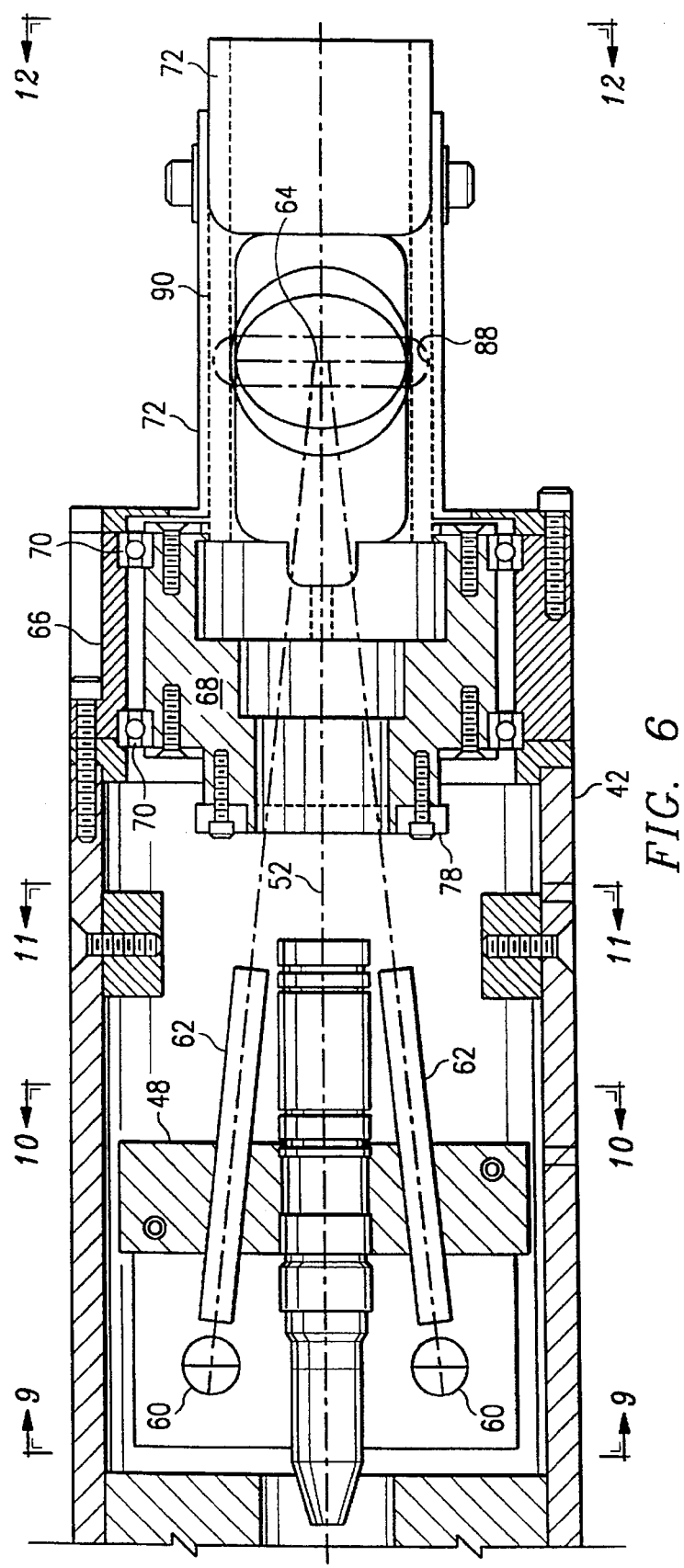
FIG. 6 is a cross-sectional view of a portion of the apparatus illustrating the camera and mirror assembly.
Figure 7:
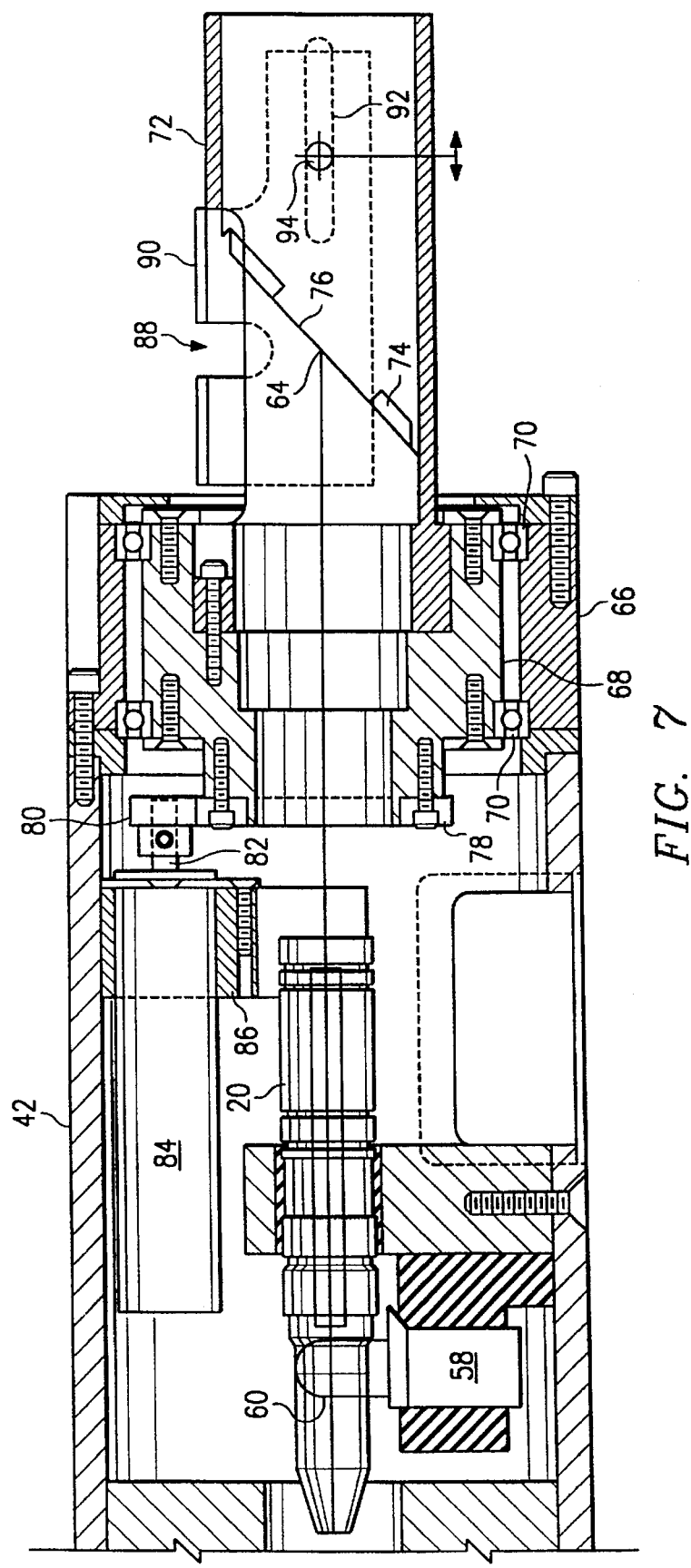
FIG. 7 is a cross-sectional view of a portion of the apparatus illustrating the camera and mirror assembly in a rotated position.
Figure 9:
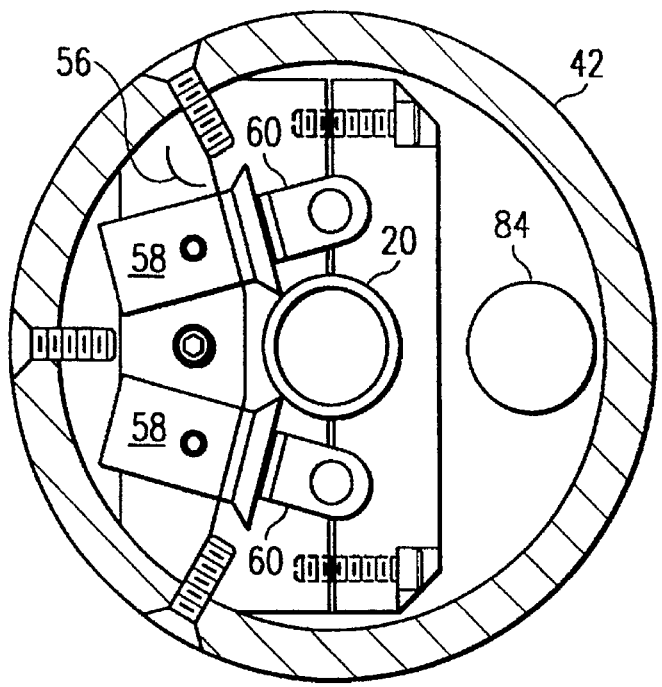
FIG. 9 is a cross-sectional view of the apparatus taken along line 9—9 in FIG. 6.
Figure 10:
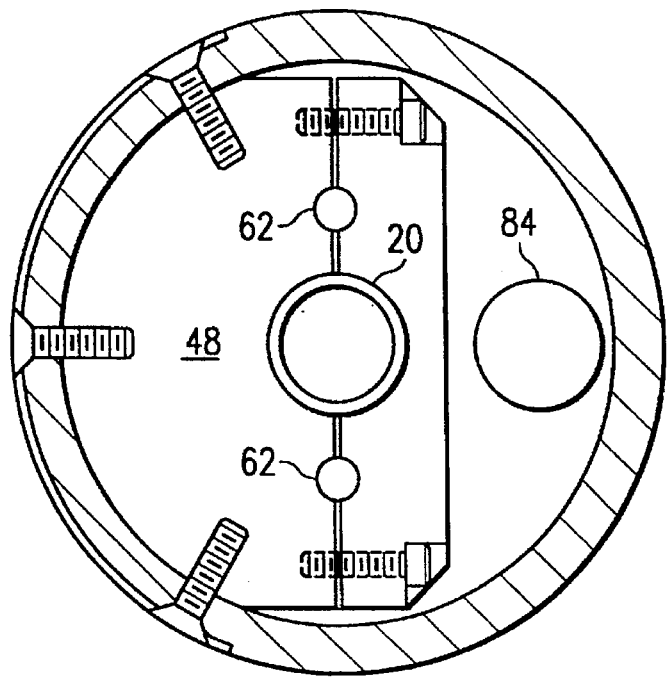
FIG. 10 is a cross-sectional view of the apparatus taken along line 10—10 in FIG. 6.
Figure 11:
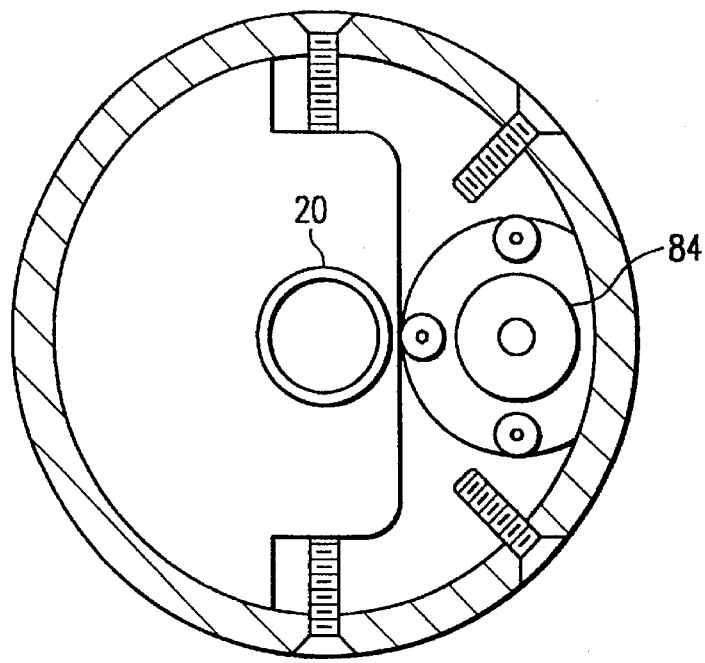
FIG. 11 is a cross-sectional view of the apparatus taken along line 11—11 in FIG. 6.
Figure 12:
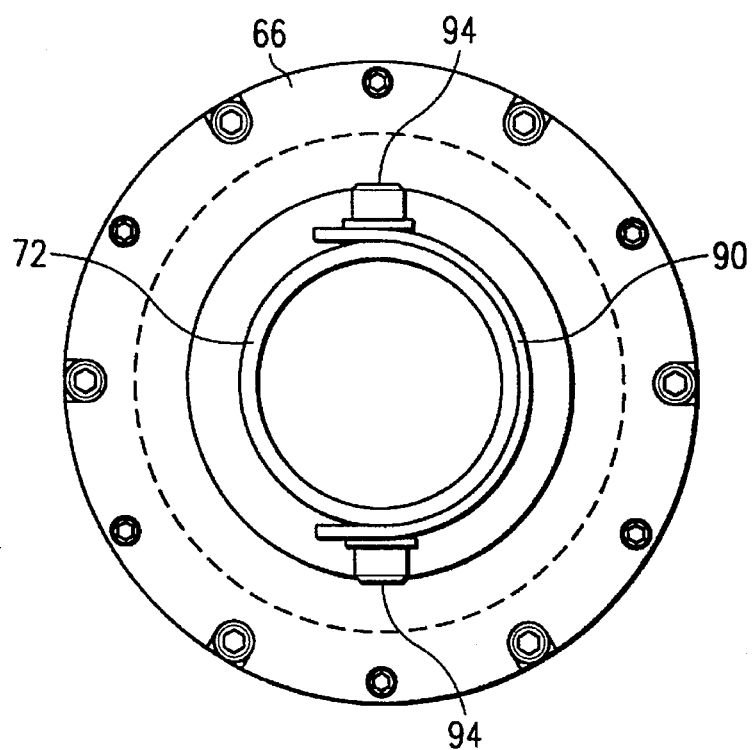
FIG. 12 is a cross-sectional view of the apparatus taken along line 12—12 in FIG. 6.

As seen in FIG. 6, a pair of light guides 62 are mounted on the assembly 48 to direct light from the lamp assemblies to a point 64 lying on the center line 52 forward of the camera.

A fixed body 66 is mounted at the forward end of the housing 42. A rotating body 68 is mounted through bearings 70 to the body 66. The bearings permit the body 68 to rotate about the center line 52 relative to the fixed body and the camera housing. Mounted to the front of the rotating body 68 is a mirror housing tube 72 which contains a mirror mount 74 for mounting an elliptical mirror 76 thereon at an angle relative to the center line 52, preferably an angle of 45°. The mirror mount is secured to the tube 72 by two bolts 94 passing through slots 92 in tube 72 that permit the mirror mount and mirror to be adjusted along center line 52 relative to tube 72 and then fixed to tube 72 by tightening bolts 94.

The mirror is a first surface instrument mirror. The mirrored surface is on the front surface of the glass to prevent double images. Conventional mirrors are mirrored on their non-viewing side. An elliptical mirror is used as the 45° angle then gives a round or circular image.

The inner end of the rotating body 68 mounts a driven gear 78. The driven gear 78 is meshed with a drive gear 80. Drive gear 80 is mounted to shaft 82 of a motor 84. The motor is mounted through a motor mount 86 to the housing 42. The motor can be operated to rotate shaft 82 in either rotational direction which, in turn, rotates the rotating body 68 and mirror 76 mounted thereon about the center line 52 to allow inspection of the entire circumference of the weld. The motor is preferably D.C. powered, controllable as to speed, direction, stopping and starting, allowing viewing of any point on the weld. An additional advantage is that none of the video cables must be twisted to inspect the circumference of the weld.

The mirror housing tube 72 mounts a sliding cover 90 which has a viewing aperture 88 through one side thereof that is in alignment with the center of the mirror. The viewing aperture 88 is sized to permit the camera to view a portion of the weld between two pipe sections. The view of the weld is reflected off the mirror at a 90° angle and along the center line 52 for viewing by the camera.

Cover 90 is supported for limited movement along the center line relative to the tube 72 by bolts 94 which pass through slots in the cover 90. This permits the portion to be viewed to be slightly adjusted. For example, the aperture can be adjusted to shape the image shown on the monitor. By changing the width of the aperture area to be viewed, the view can be limited to the weld area only or to the weld and adjacent areas.

As seen in FIG. 5, the apparatus 18 can be centered within the pipe by use of guide arms 96 pivoted at one end to the coupling 44 and urged into engagement with the interior surface of the adjacent pipe section by springs 98. Rollers 100 at the ends of the arms 96 reduce the frictional engagement between the arms and the pipe section wall.

Figure 13:
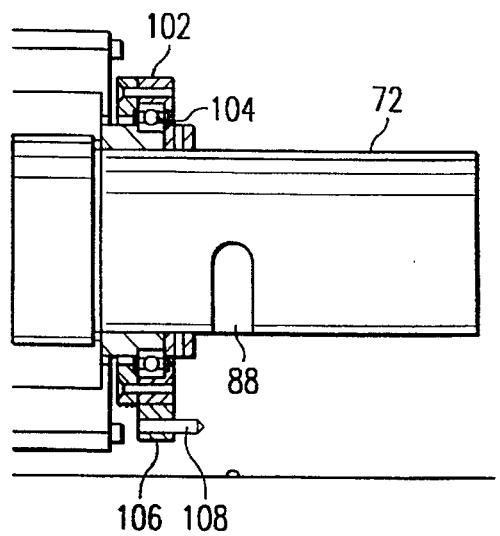
FIG. 13 is a detail view of a mirror alignment structure.
Figure 14:
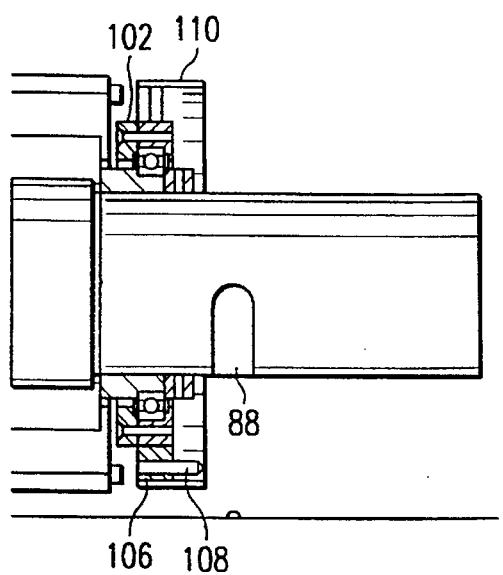
FIG. 14 is a detail view of an alternate mirror alignment structure with a scale.
Figure 15:
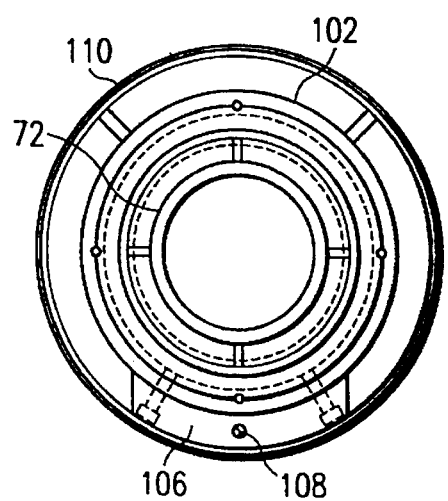
FIG. 15 is an end view of the mirror alignment structure.

With reference to FIGS. 13–15, a pendulum ring 102 can be mounted through bearing 104 on the tube 72. In the embodiment shown in FIG. 13, the ring 102 mounts a pendulum weight 106 on one side thereof, which in turn mounts an indicating pin 108 which extends into the field of vision of the TV camera viewing through the aperture 88. Any misalignment can be corrected by loosening bolts 94 and moving mirror mount 74 and mirror 76 along the center line 52, adjusting cover 90, if necessary, and retightening bolts 94. The weight 106 causes the ring 102 to rotate on tube 72 and maintains the pin at the bottom of the apparatus at all times so that the TV camera can orient the picture being viewed relative to the position on the interior surface of the welded pipe sections.

FIGS. 14 and 15 illustrate a variation where a continuous 360° scale 110 is mounted on the ring 102 in addition to the pin 108. The scale, which can be marked with degrees about the entire circumference thereof, will be in the view of the TV camera to permit an exact orientation to be made of the portion of the well being viewed. The scale can also be marked in clock position, or "top", "side 1", "bottom" and "side 2" (this is important when locating position of possible weld defects shown on N.D.T.-X-ray, etc.).

Figure 16:
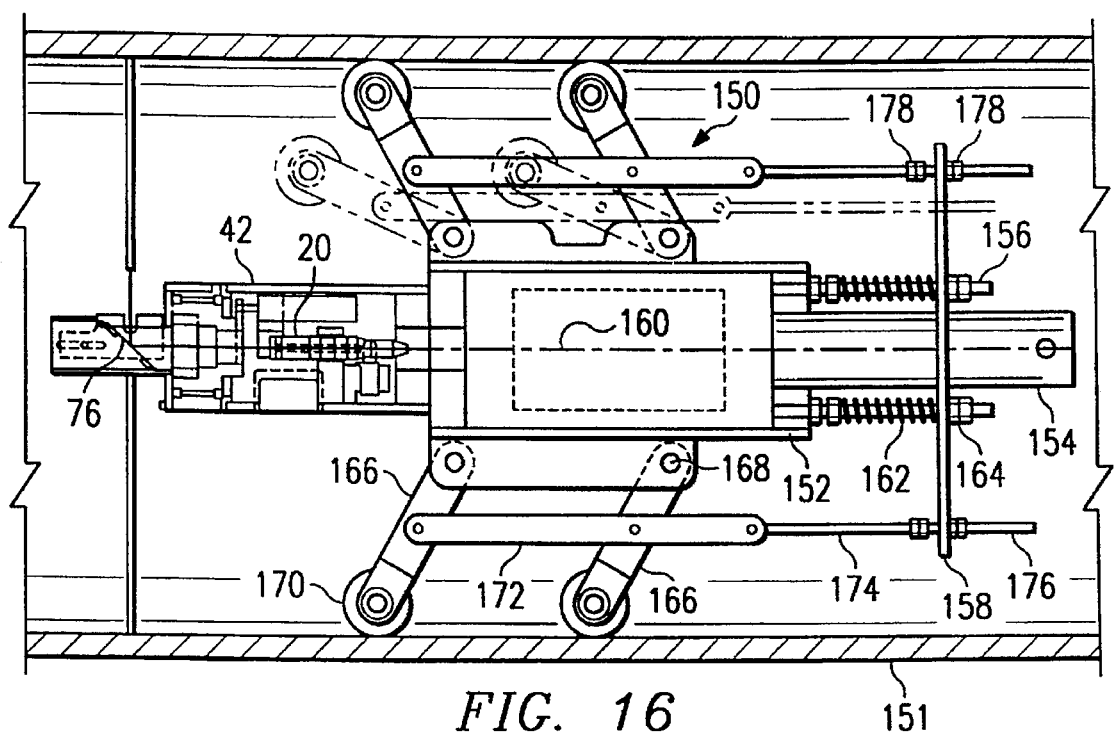
FIG. 16 is a side view of a visual inspection apparatus forming a second embodiment of the present invention for large diameter pipeline.
Figure 17:
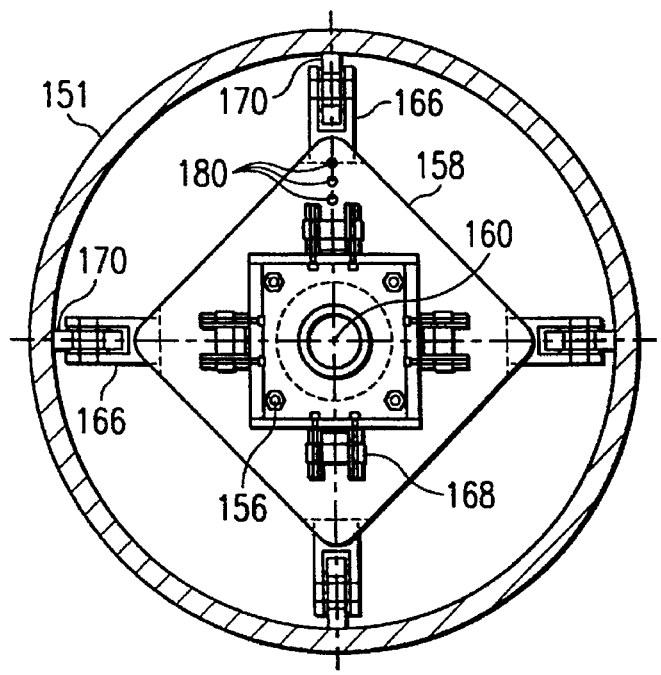
FIG. 17 is an end view of the apparatus of FIG. 16.

With reference now to FIGS. 16 and 17, an apparatus 150 is illustrated which is intended for use in larger diameter pipelines formed of pipe sections 151 for inspecting welds between abutting pipe sections. The apparatus includes a body 152 which mounts at one end thereof a camera and drive housing 42, including a TV camera 20, mirror 76 and other structure described previously with respect to apparatus 18. At the other end of the body is mounted a housing 154 which preferably contains the camera control unit 32. A series of four threaded rods 156 extend from the side of the body about the housing 154 which support a plate 158 thereon for limited movement along the center axis 160 of the apparatus. A spring 162 is mounted on each rod between the body 152 and plate 158 to urge the plate to the rightward as seen in FIG. 16. Adjustment nuts 164 are threaded onto the rods 156 to limit the motion of the plane 154 in the rightward direction as seen in FIG. 16.

On the body 152 are mounted four pairs of arms 166, with the inner end of each arm pivoted at a hinge 168 to the body. The outer ends of the arms mount a wheel 170 for contacting the inner surface of the pipe section 151. The pairs of arms are distributed at equal angles around the circumference of the apparatus, preferably 90° relative to the adjacent pairs. A connecting arm 172 is pivoted between the midsection of each arm in a given pair and is connected to the plate 158 through a rod 174 with a threaded portion 176. A series of nuts 178 allow the rod 174 to be adjusted relative to the plate.

As can be readily understood, the force of the springs 162 is sufficient to urge the plate 158 in the rightward direction in FIG. 16. This motion, in turn, is conveyed through rods 174 to pivot the arms 166 to engage the wheels 170 thereof against the inner surface of the pipe section 151 to center the apparatus 150 along the center line 160 of the pipeline. Preferably, a series of holes 180 are drilled in plate 158 to receive rods 174 along a radial line from center line 160 which allow the rods 174 to pass through an appropriate hole for the given diameter of pipe. This makes the apparatus 150 adaptable readily for use with different diameter pipes within the ranges permitted by the number of holes 180.

As noted above, apparatus 18 need not be used with pipe clamp 12. It can be used independently or pulled behind larger clamps or internal welders. It can also be inserted with suitable guides into valves, fittings, tubular members, connections, or any other structure where remote viewing is useful to visually inspect an area. For larger pipes, differently mounted light sources can be used so that, depending on distance (pipe diameter) etc., optimum illumination of the weld area can be obtained.

Although the present invention has been described with respect to a specific preferred embodiment thereof, various changes and modifications may be suggested to one skilled in the art, and it is intended that the present invention encompass such changes and modifications as fall within the scope of the appended claims.

I claim:

1. A device for inspecting welds between pipe sections in a pipeline, comprising:

a member sized for insertion within the interior of the pipe section;

a camera mounted on the member, the lens of the camera aligned with the elongate axis of the pipeline;

a mirror assembly mounted on the member, the mirror assembly mounting a mirror to reflect the image of a portion of the weld along the elongate axis of the pipeline into the lens of the camera.

2. The device of claim 1 further comprising a light source to illuminate the portion of the weld being viewed.

3. A device for inspecting welds between pipe sections in a pipeline, comprising:

a member sized for insertion within the interior of the pipe section;

a camera mounted on the member, the lens of the camera aligned with the elongate axis of the pipeline;

a mirror assembly mounted on the member, the mirror assembly mounting a mirror to reflect the image of a portion of the weld along the elongate axis of the pipeline into the lens of the camera;

the mirror assembly having a mechanism to rotate the mirror about the elongate axis to examine the entire circumference of the weld.

4. A device for inspecting welds between pipe sections in a pipeline, comprising:

a member sized for insertion within the interior of the pipe section;

a camera mounted on the member, the lens of the camera aligned with the elongate axis of the pipeline;

a mirror assembly mounted on the member, the mirror assembly mounting a mirror to reflect the image of a portion of the weld along the elongate axis of the pipeline into the lens of the camera;

the mirror being angled at 45° relative to the elongate axis of the pipeline.

5. The device of claim 2 further comprising a light guide tube mounted on the member for focusing light from the light source on the portion of the weld being viewed.

6. A device for inspecting welds between pipe sections in a pipeline, comprising:

a member sized for insertion within the interior of the pipe section;

a camera mounted on the member, the lens of the camera aligned with the elongate axis of the pipeline;

a mirror assembly mounted on the member, the mirror assembly mounting a mirror to reflect the image of a portion of the weld along the elongate axis of the pipeline into the lens of the camera;

an indicator for indicating the position of the weld being viewed relative to the vertical.

7. The device of claim 1 further comprising an expandable pipe clamp mounted in the member for clamping adjacent pipe sections together to weld the pipe sections together.

8. The device of claim 1 wherein the mirror assembly includes a fixed body and a rotating body mounted through bearings to the fixed body, the mirror mounted on the rotating body for rotation about the elongate axis of the pipeline.

9. The device of claim 8 further comprising a motor for rotating the rotating body.

10. The device of claim 1 wherein the mirror assembly further includes a sliding cover with a viewing aperture therein, the image of the portion of the weld passing through the viewing aperture.

11. The device of claim 1 further comprising extendable guide arms to center the lens of the camera along the elongate axis of the pipeline.

12. The device of claim 11 wherein the guide arms are spring-loaded radially outward to contact the inner surface of the pipeline.

13. The device of claim 6 wherein the indicator includes a pendulum weight mounted for rotational motion about the elongate axis of the pipeline to maintain a portion of the indicator fixed relative to the vertical.

14. The device of claim 6 wherein the indicator is a pin.

15. The device of claim 6 wherein the indicator is a scale.

16. The device of claim 1 wherein the mirror is elliptical.

17. The device of claim 10 wherein the sliding cover is moveable along the elongate axis of the pipeline.

* * * * *